US012599727B2

(12) United States Patent
Nalawade

(10) Patent No.: US 12,599,727 B2
(45) Date of Patent: Apr. 14, 2026

(54) SYRINGE WITH SUCTION-BASED AUTOMATIC DISABLING

(71) Applicant: Becton, Dickinson and Company, Franklin Lakes, NJ (US)

(72) Inventor: Praveen Nalawade, Belagavi (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 773 days.

(21) Appl. No.: 17/979,430

(22) Filed: Nov. 2, 2022

(65) Prior Publication Data

US 2024/0139437 A1 May 2, 2024

(51) Int. Cl.
 *A61M 5/50* (2006.01)
 *A61M 5/31* (2006.01)
 *A61M 5/315* (2006.01)
(52) U.S. Cl.
 CPC .......... *A61M 5/504* (2013.01); *A61M 5/3134* (2013.01); *A61M 5/31515* (2013.01); *A61M 2207/10* (2013.01)
(58) Field of Classification Search
 CPC ................ A61M 5/504; A61M 5/3134; A61M 5/31515; A61M 5/31513; A61M 2005/31521
 See application file for complete search history.

(56) References Cited

U.S. PATENT DOCUMENTS 3,740,856 A 6/1973 Culver et al.
4,775,364 A 10/1988 Alles 4,986,820 A * 1/1991 Fischer ............. A61M 5/31513
                                                    604/218
5,176,639 A 1/1993 Pozzi et al.
6,017,330 A * 1/2000 Hitchins ........... A61M 5/14546
                                                    604/152
8,287,491 B2 10/2012 Bums et al.
8,574,202 B2 11/2013 Alheidt
10,850,085 B2 12/2020 Tekeste
2003/0035744 A1 2/2003 Horita et al.
2003/0225358 A1 12/2003 Berman et al.
(Continued)

FOREIGN PATENT DOCUMENTS

WO 9711728 A1 4/1997

OTHER PUBLICATIONS

"Design of the Suction Cup", Schmalz, Website, https://www.schmalz.com/en/vacuum-knowledge/the-vacuum-system-and-its-components/vacuum-suction-cups/design-of-the-suction-cup/.
(Continued)

*Primary Examiner* — Tasnim Mehjabin Ahmed
(74) *Attorney, Agent, or Firm* — The Webb Law Firm

(57) ABSTRACT

Provided herein is a syringe including a syringe barrel having a barrel proximal end and a barrel distal end and defining a chamber configured for containing a fluid therein. The syringe also includes a plunger axially movable within the chamber of the syringe barrel, the plunger having a plunger proximal end and a plunger distal end. The syringe further includes a stopper secured to the plunger distal end, the stopper axially movable with the plunger within the chamber, with the stopper having an attachment member configured to couple to the plunger distal end and a cup member extending out distally from the attachment member, the cup member having a concave shape.

20 Claims, 5 Drawing Sheets

(56) References Cited

U.S. PATENT DOCUMENTS

| | | | | |
|---|---|---|---|---|
| 2005/0054979 A1* | 3/2005 | Liu | ..................... | A61M 5/3243 |
| | | | | 604/110 |
| 2008/0300551 A1* | 12/2008 | Schiller | ............ | A61M 5/31513 |
| | | | | 604/220 |

OTHER PUBLICATIONS

Gautriaud et al., "Effect of Sterilization on the Mechanical Properties of Silicone Rubbers", Saint-Gobain Performance Plastics, 2009, pp. 1-9, Website, https://www.biopharm.saint-gobain.com/sites/imdf.biopharm.com/files/effect-of-sterilization-on-the-mechanical-properties-of-silicone-rubbers.pdf.

Gautriaud et al., "Effect of Sterilization on the Mechanical Properties of Silicone Rubbers", BioProcess International, 2010, Website, https://bioprocessintl.com/manufacturing/monoclonal-antibodies/effect-of-sterilization-on-the-mechanical-properties-of-silicone-rubbers-239379/.

"Keys To Applying Vacuum Systems", Design World, 2012, Website, https://www.designworldonline.com/keys-to-applying-vacuum-systems/.

Korane, "How do you size a vacuum cup?", PneumaticTips, 2016, Website, https://www.pneumatictips.com/size-vacuum-cup/.

"Silicone Sterilization", TBL Performance Plastic Company, a SaniSure Company, Website, https://www.tblplastics.com/sterilize-platinum-peroxide-cured-silicone/.

"Simplex Auto Disable Safety Syringe", Panamed Philippines Inc., 2017, YouTube Video, https://www.youtube.com/watch?v=7_ePON9kJcE.

"What's the best SPI surface finish for your injection molded part?" Hubs: a Protolabs Company, Website, https://www.3dhubs.com/knowledge-base/injection molding-spi-surface-finishes/.

* cited by examiner

SYRINGE WITH SUCTION-BASED AUTOMATIC DISABLING

BACKGROUND OF THE INVENTION

Field of the Invention

The present disclosure relates generally to syringes and, more specifically, to single-use syringes with features for automatically disabling repeated use of the syringe.

Description of Related Art

Syringes are used in a variety of environments for administering liquids, such as medicaments, to a patient. Many syringes are designed as single-use devices that are to be discarded after use. The re-use of such single-use syringes, such as may occur at high rates in developing countries, may lead to the transmission of various blood-borne diseases and/or pathogens, including hepatitis and HIV, as examples.

Many single-use syringes have been designed to remedy the problem of unauthorized re-use by being designed to be inoperative after an initial use of the syringe. Some of these single-use syringes may include a locking element or feature positioned in the syringe barrel and/or on the plunger of the syringe, with the locking element preventing retraction of the plunger after injection/administering of a fluid to a patient. Other single-use syringes may include an added locking element separate from the syringe barrel and plunger that prevents retraction of the plunger after injection/administering of a fluid to a patient. In either design, the locking element or feature typically increases the cost and/or complexity of the manufacturing and assembly processes of the syringe, such as by requiring either intricate molded components or additional assembly steps during manufacturing.

Accordingly, a need exists in the art for single-use syringes that effectively disable the syringe after an initial use so as to prevent re-use thereof, but that are manufacturable at low cost and with minimal assembly steps.

SUMMARY OF THE INVENTION

Provided herein is a syringe including a syringe barrel having a barrel proximal end and a barrel distal end and defining a chamber configured for containing a fluid therein. The syringe also includes a plunger axially movable within the chamber of the syringe barrel, the plunger having a plunger proximal end and a plunger distal end. The syringe further includes a stopper secured to the plunger distal end, the stopper axially movable with the plunger within the chamber, with the stopper having an attachment member configured to couple to the plunger distal end and a cup member extending out distally from the attachment member, the cup member having a concave shape.

In some embodiments, the syringe barrel includes a cylindrical outer wall extending between the barrel proximal end and the barrel distal end, an end wall positioned at the barrel distal end, and a nozzle extending distally from the end wall, the nozzle defining a lumen through which fluid enters into or exits from the chamber, with an inner surface of the end wall having a generally flat surface.

In some embodiments, the cup member is composed of a flexible material, such that cup member is deflectable between the concave shape and a flat shape In some embodiments, the stopper includes a nose member extending out distally past the cup member, the nose member positioned within a circumference of the cup member.

In some embodiments, the plunger and the stopper coupled thereto, are movable from a retracted position where the cup member and the nose member are axially separated from the end wall to an advanced position where the cup member is in contact with the end wall and the nose member extends into the nozzle.

In some embodiments, with the plunger and the stopper in the advanced position, the nose member extends into the nozzle and the cup member deflects from the concave shape to the flat shape, thereby creating a suction between the stopper and the end wall of the syringe barrel.

In some embodiments, with the plunger and the stopper in the advanced position, the stopper is suctioned to the end wall with a suction force that is greater than a coupling force that couples the stopper to the plunger.

In some embodiments, the plunger distal end includes a flanged extension member and the attachment member of the stopper comprises a receptacle formed therein, with the flanged extension member coupling with the receptacle via a press fit connection, to secure the stopper to the plunger.

In some embodiments, with the stopper suctioned to the end wall with the suction force, the flanged extension member is pulled out of the receptacle when a proximally directed pulling force is applied to the plunger that is greater than the coupling force, thereby separating the stopper from the plunger.

In some embodiments, with the stopper separated from the plunger, the stopper is trapped at the advanced position, thereby preventing re-use of the syringe.

In some embodiments, the inner surface of the end wall includes a surface finish thereon that increases the suction between the cup member and the end wall.

In some embodiments, the syringe barrel comprises a retaining ring formed on an interior surface thereof, the retaining ring positioned toward the barrel proximal end, and wherein the plunger comprises an annular rib formed thereon positioned toward the plunger proximal end, with the annular rib proximal from the retaining ring when the plunger and the stopper are in the retracted position.

In some embodiments, to move the plunger and stopper to the advanced position, a distally directed force applied to the plunger must be greater than a friction force between the annular rib and the retaining ring.

Also provided herein is a method of manufacturing a syringe as previously described. The method includes providing the syringe barrel, securing the stopper to the plunger by coupling the attachment member to the plunger distal end, and positioning the stopper and a portion of the plunger within the chamber of the syringe barrel. In positioning the stopper and the portion of the plunger within the chamber, the plunger and the stopper are put into an initial position, where the cup member is separated from the barrel distal end.

Also provided herein is a syringe including a syringe barrel having a barrel proximal end and a barrel distal end and defining a chamber configured for containing a fluid therein. The syringe also includes a plunger assembly axially movable within the chamber of the syringe barrel between a retracted position and an advanced position, with the plunger assembly further including a plunger having a plunger proximal end and a plunger distal end and a stopper secured to the plunger distal end, the stopper configured to suction to the barrel distal end upon the plunger assembly being moved to the advanced position. The stopper is further configured to separate from the plunger and remain suctioned to the barrel distal end upon the plunger being moved axially from the advanced position back toward the retracted position.

In some embodiments, the stopper includes an attachment member configured to couple to the plunger distal end, a cup member extending out distally from the attachment member and having a concave shape, with the cup member being deflectable between the concave shape and a flat shape, and a nose member extending out distally from the attachment member and past the cup member, the nose member positioned within a circumference of the cup member.

In some embodiments, the plunger distal end includes a flanged extension member and the attachment member of the stopper includes a receptacle formed therein, with the flanged extension member coupling with the receptacle via a press fit connection, to secure the stopper to the plunger. With the stopper suctioned to the barrel distal end, the flanged extension member is pulled out of the receptacle when the plunger is moved axially from the advanced position back to the retracted position.

In some embodiments, the syringe barrel includes a cylindrical outer wall extending between the barrel proximal end and the barrel distal end, an end wall positioned at the barrel distal end, and a nozzle extending distally from the end wall, the nozzle defining a lumen through which fluid enters into or exits from the chamber, with an inner surface of the end wall having a generally flat surface.

In some embodiments, with the plunger assembly in the advanced position, the nose member extends into the nozzle and the cup member contacts the end wall and deflects from the concave shape to the flat shape, thereby suctioning the stopper to the end wall of the syringe barrel.

In some embodiments, the syringe barrel includes a retaining ring formed on an interior surface thereof, the retaining ring positioned toward the barrel proximal end, and the plunger includes an annular rib formed thereon positioned toward the plunger proximal end, with the annular rib proximal from the retaining ring when the plunger and the stopper are in the retracted position. To move the plunger and stopper to the advanced position, a distally directed force applied to the plunger assembly must be greater than a friction force between the annular rib and the retaining ring.

DESCRIPTION OF THE INVENTION

Figure 1:
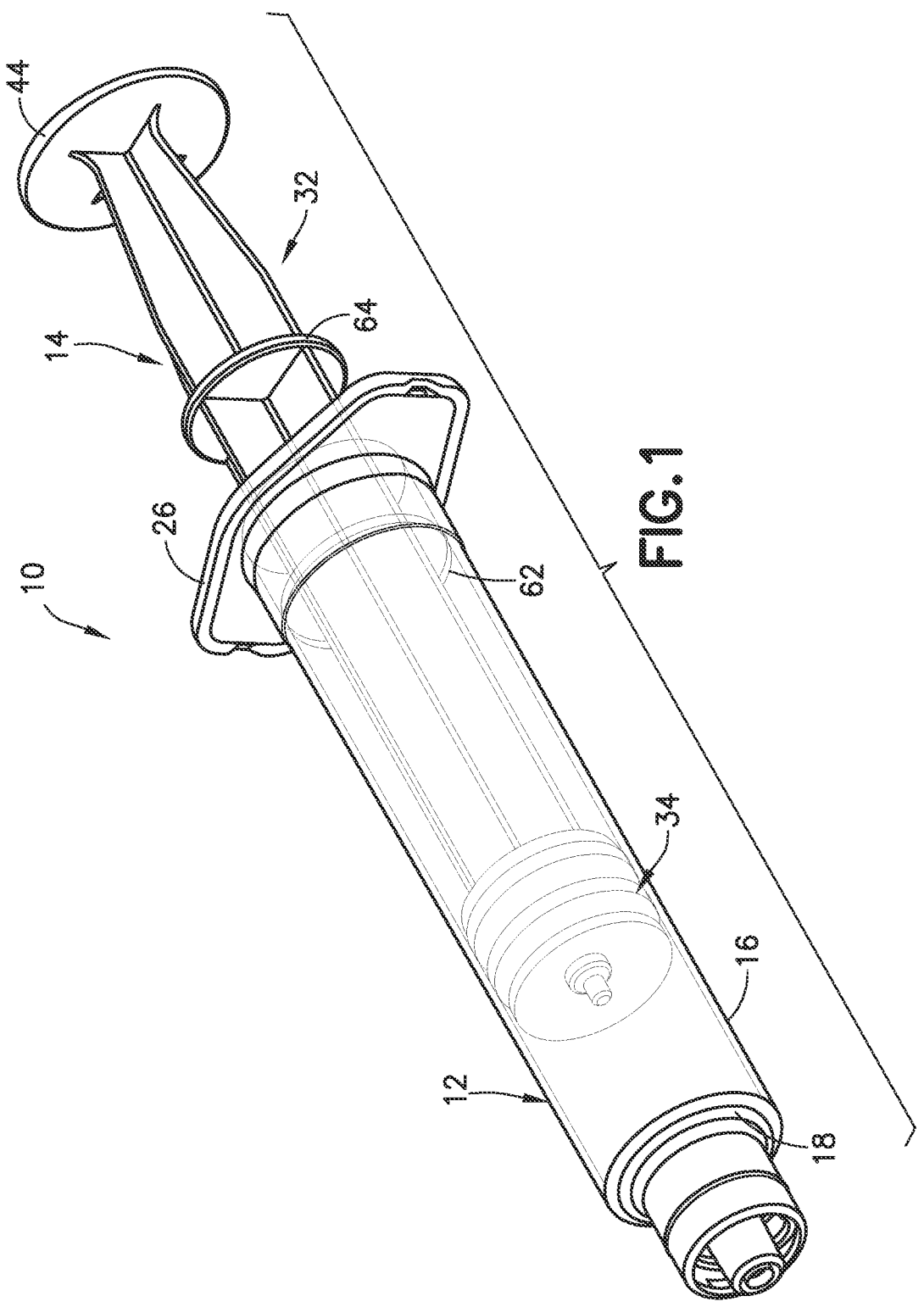
FIG. 1 is a perspective view of a syringe, according to a non-limiting embodiment described herein.
Figure 2:
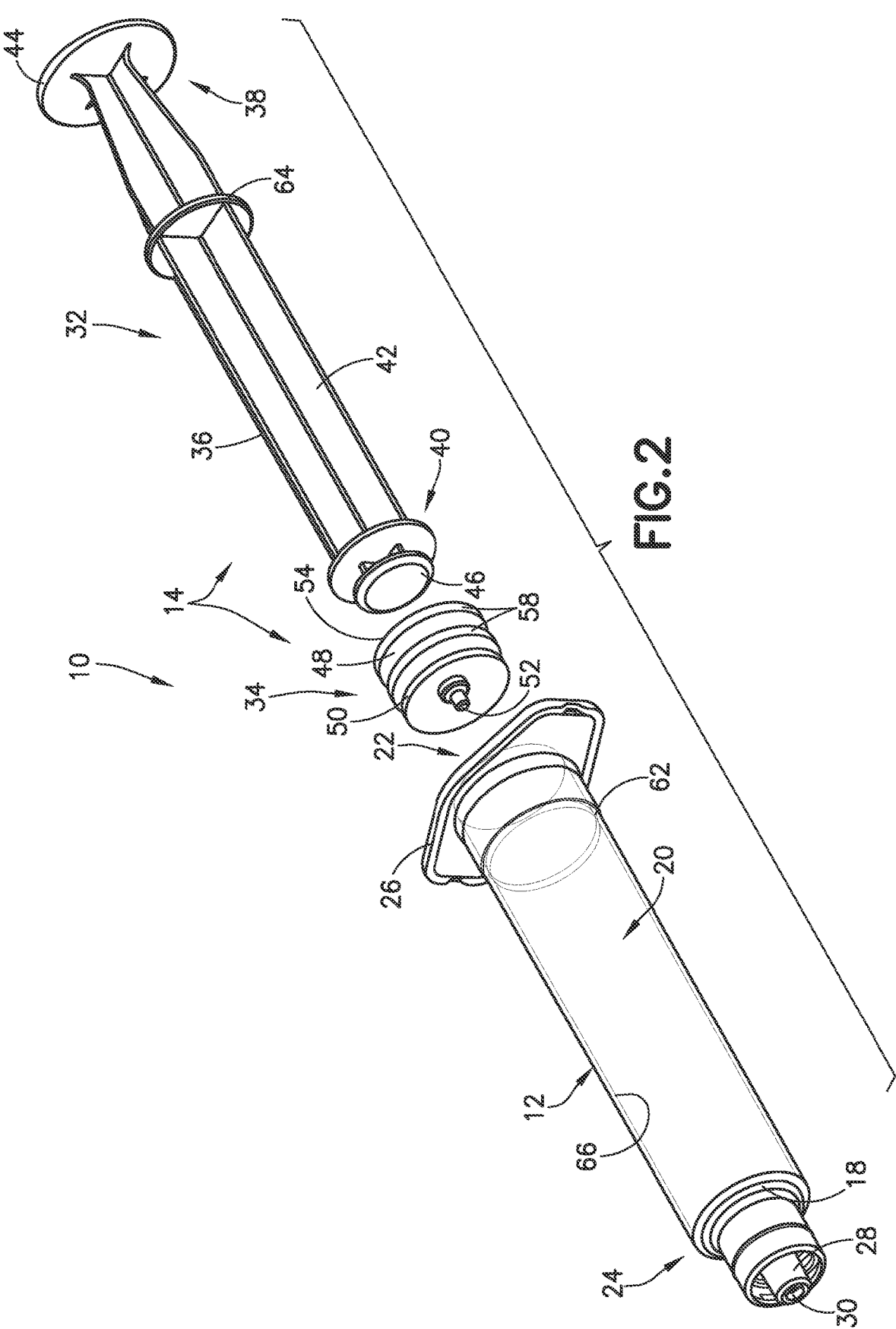
FIG. 2 is an exploded view of the syringe of FIG. 1.
Figure 3:
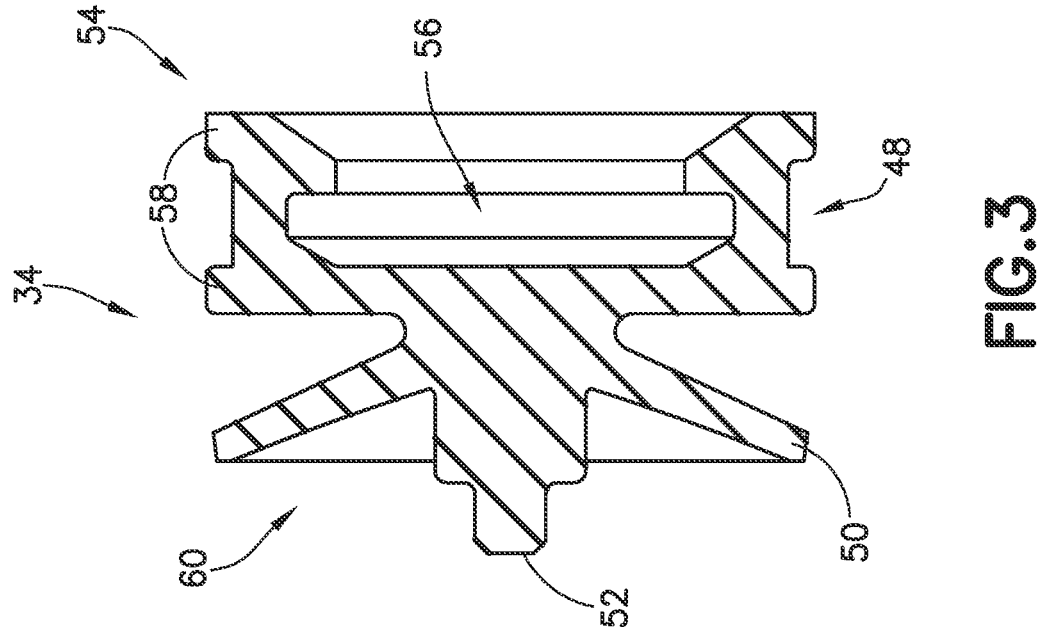
FIG. 3 is a side cross-sectional view of a stopper included in the syringe of FIG. 1.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device being manipulated by the user would be the proximal end of the device.

The terms "first", "second", and the like are not intended to refer to any particular order or chronology, but refer to different conditions, properties, or elements.

Referring to FIGS. 1-7, shown is a non-limiting embodiment of a single-use syringe 10. The syringe 10 generally includes a syringe barrel 12 and a plunger assembly 14. The plunger assembly 14 is axially movable within the syringe barrel 12 between a retracted position (FIG. 5) and an advanced position (FIG. 6) to facilitate administering of an injectable fluid (e.g., medication) to a patient, for example.

The syringe barrel 12 is formed of a generally cylindrical outer wall 16 and an end wall 18 that collectively define a chamber 20 for retaining fluid. The syringe barrel 12 includes an open proximal end 22 configured to receive the plunger assembly 14 therein and a distal end 24 at which end wall 18 is positioned. The proximal end 22 of the syringe barrel 12 may include a flange 26 to facilitate handling and positioning of the syringe 10 and to maintain the relative position of the syringe barrel 12 with respect to the plunger assembly 14 during medication administration. At the distal end 24, a nozzle 28 extends distally outward from the end wall 18 and defines a lumen 30 in fluid communication with the chamber 20. In some embodiments, the nozzle 28 may be configured as a luer connection (male luer connection) that is coupleable to a corresponding needle-free connector (not shown) to which the syringe 10 is to be brought into engagement for administering medication to a patient. It can be appreciated that other types of attachment arrangements can be provided for securing the distal end 24 of the syringe barrel 12 for expelling the injectable material into a target location.

The plunger assembly 14 of syringe 10 is formed of an elongate plunger rod 32 (more generally "plunger 32," as used hereafter) and a plunger head or stopper 34. The plunger 32 may include a main body 36 extending between a plunger proximal end 38 and a plunger distal end 40. In some embodiments, the main body 36 may include a plurality of elongate vanes or walls 42 extending axially along a length thereof between the plunger proximal end 38 and the plunger distal end 40. A thumb press 44 is positioned at the plunger proximal end 38 that may be engaged by a thumb (or other finger) of the user to apply a distally directed force to the plunger assembly 14 to move the plunger 32 with respect to the syringe barrel 12. In some embodiments, a flanged extension member 46 (e.g., disc-shaped flange) is positioned at the plunger distal end 40 that is configured to mate with the stopper 34.

The stopper 34 of plunger assembly 14 is positioned at the plunger distal end 40 so as to be movable along with the plunger 32 within the chamber 20 of syringe barrel 12. The stopper 34 may be made from a material that is different from the material of the plunger 32, with the stopper 34 being formed of a flexible, elastomeric material, for example, that is capable of forming a tight seal with the syringe barrel 12 as it is advanced therethrough. The stopper 34 may be generally defined as including an attachment member 48, a cup member 50 and a nose member 52. The attachment member 48 is provided at a proximal end 54 of the stopper 34 and is configured to mate with the plunger 32. In some embodiments, the attachment member 48 includes a receptacle 56 (FIG. 3) formed therein that is sized and configured to receive the flanged extension member 46 of plunger 32, with the flanged extension member 46 coupling with the receptacle 56 via a press fit connection, for example, to secure the stopper 34 to the plunger 32, although it can be appreciated that the attachment member 48 and plunger distal end 40 can be secured by other techniques known in the art. The attachment member 48 may further include a pair of spaced-apart annular flanges 58 formed thereon (i.e., O-rings) that form a tight seal with the cylindrical outer wall 16 of syringe barrel 12.

The cup member 50 extends distally away from attachment member 48 so as to face toward the end wall 18 of the syringe barrel 12. The cup member 50 is configured to have a concave shaped distally facing surface 60. As indicated above, the stopper 34—including cup member 50—is formed of a flexible material, such that the cup member 50 is deformable and may change from having a concave shape to having a generally flat profile or shape when pressure is applied thereto. In some embodiments, the cup member 50 may be formed to have a slightly smaller diameter than that of the attachment member 48 (i.e., of the O-rings 58 of attachment member 48), such that the cup member 50 does not form a tight seal with the cylindrical outer wall 16 of syringe barrel 12.

The nose member 52 extends distally away from attachment member 48 and out past the cup member 50 of stopper 34. The nose member 52 is positioned within the circumference of the cup member 50 and is centered on the stopper 34, such that the nose member 52 is aligned with the nozzle 28 of syringe barrel 12. The nose member 52 is sized and configured to mate with the nozzle 28 when the plunger assembly 14 is moved axially to the advanced position, with the nose member 52 forming a seal with the nozzle 28 when mated therewith.

According to aspects of the disclosure, the syringe 10 is configured to include an automatic disabling feature incorporated therein that prevents re-use of the syringe 10 after an initial use thereof—i.e., after an initial administering of medication out from the syringe 10. Specifically, the cup member 50 of stopper 34 is configured to form a suction-type engagement with the end wall 18 of the syringe barrel 12 when the plunger assembly 14 is actuated to the advanced position. With the cup member 50 suctioned to the end wall 18 of the syringe barrel 12, a subsequent attempt to actuate the plunger assembly 14 back to the retracted position (i.e., by applying a proximally directed force to the plunger 32) will cause the stopper 34 to detach and separate from the plunger 32. Upon detaching from the plunger 32, the stopper

34 becomes trapped at the advanced position, thereby limiting use of the syringe 10 to a single/initial use and disabling the syringe 10 from use in a subsequent injection application.

Figures 4, 5:
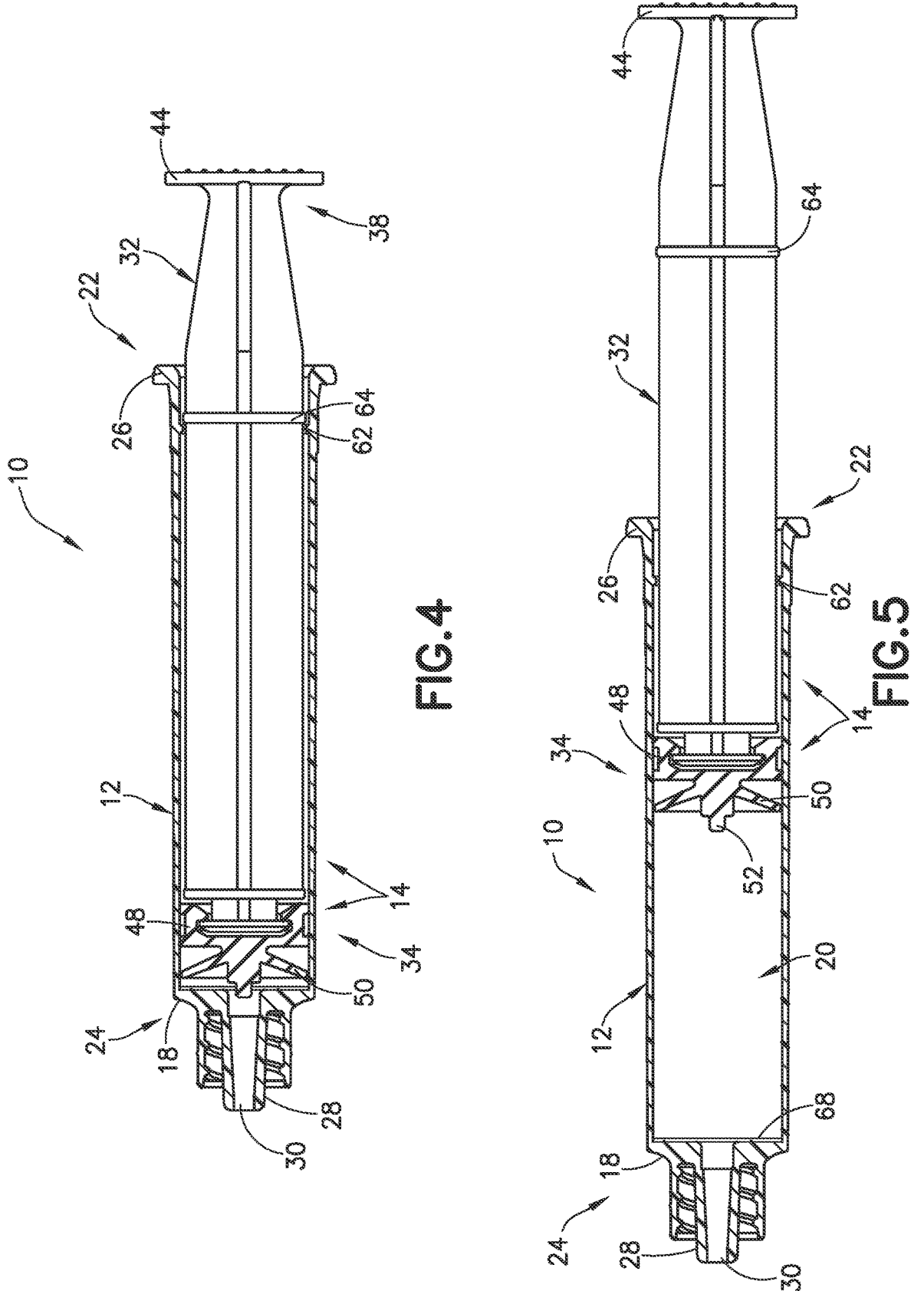
FIG. 4 is a side cross-sectional view of the syringe of FIG. 1, with the plunger assembly in an initial or pre-use position.
FIG. 5 is a side cross-sectional view of the syringe of FIG. 1, with the plunger assembly in a retracted position, prior to an initial use.

Referring to FIGS. 4-7, the syringe 10 is illustrated in its various stages of use or actuation, to better explain and show the automatic disabling feature of the syringe 10. Referring first to FIG. 4, the syringe 10 is shown in its initial or pre-use position, such as would be present upon an unpacking of the syringe 10. In its initial position, the plunger assembly 14 of the syringe 10 is located within the syringe barrel 12 at a location between the fully retracted and fully advanced positions previously referenced. In the initial position, the stopper 34 is spaced apart from the end wall 18 of the syringe barrel 12, such that the cup member 50 of stopper 34 is not in contact with the end wall 18 (and cannot become suctioned to the end wall 18). According to some embodiments, a retaining ring 62 and an annular rib 64 are provided on the syringe barrel 12 and the plunger 32, respectively, which function to maintain the syringe 10 in its initial position and prevent accidental actuation to the advanced position. The retaining ring 62 is formed on an interior surface 66 of the syringe barrel 12, toward the proximal end 22 thereof, and the annular rib 64 is similarly formed on the plunger 32 toward the proximal end 38 thereof, with the annular rib 64 proximal from the retaining ring 62 when the plunger assembly 14 is in the initial position. The retaining ring 62 and annular rib 64 maintain the syringe 10 in its initial position, as a distally directed force is required to be applied to the plunger assembly 14 in order to slide the annular rib 64 distally past the retaining ring 62 and thereby move the plunger assembly 14 to the advanced position (i.e., a distally directed force must be applied to the plunger assembly 14 that is greater than a friction force between the annular rib 64 and the retaining ring 62).

As shown in FIG. 5, the syringe 10 may be drawn back from the initial position to its retracted position, to allow a clinician to aspirate medication into the syringe barrel 12. The clinician may apply a proximally directed force to the plunger assembly 14, such as by gripping and applying pressure on the flange 26 of syringe barrel 12 and/or the thumb press 44 on plunger 32, thereby causing the plunger 32 and stopper 34 to withdraw back to the retracted position.

Figures 6, 7:
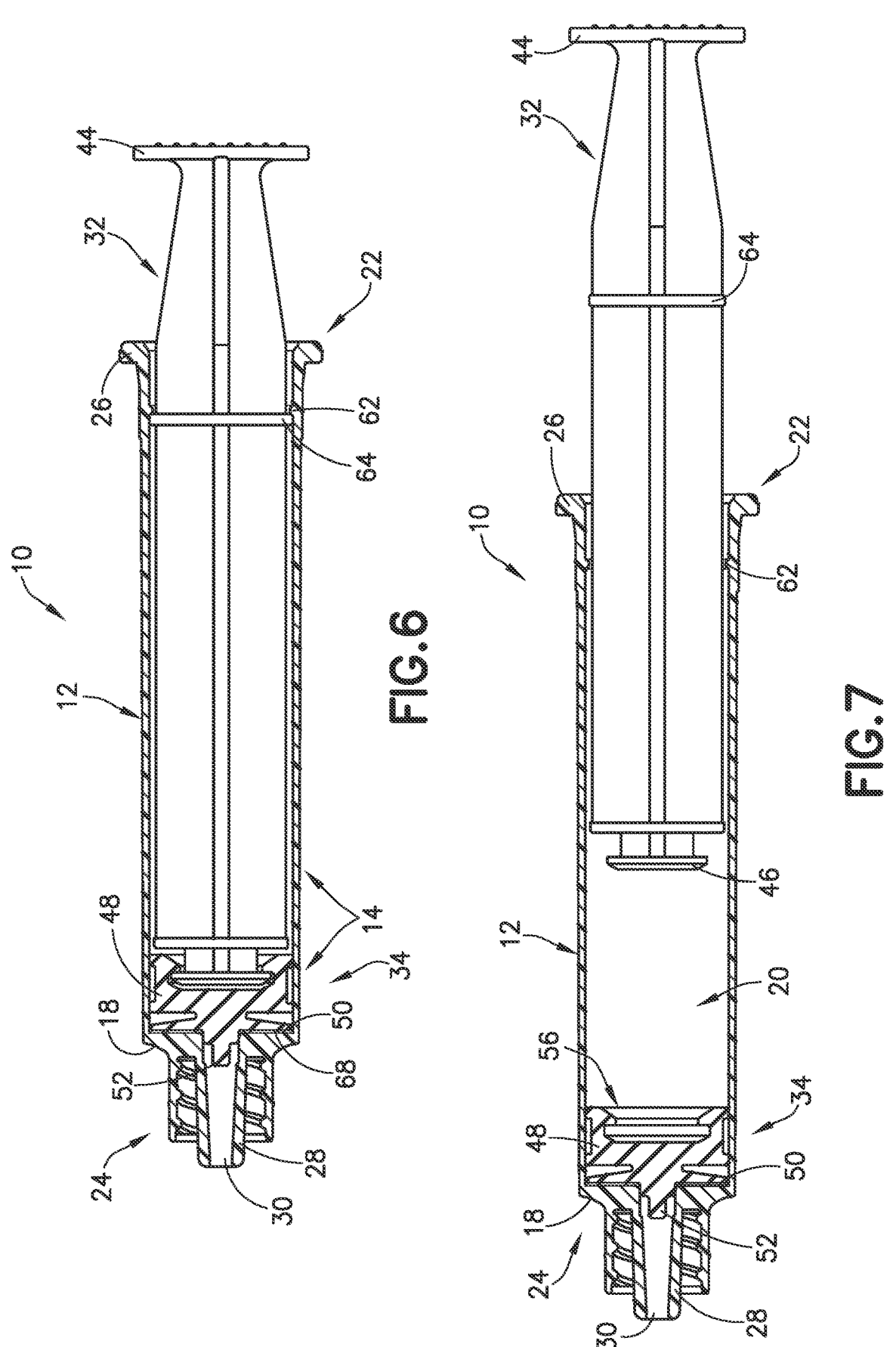
FIG. 6 is a side cross-sectional view of the syringe of FIG. 1, with the plunger assembly in an advanced position.
FIG. 7 is a side cross-sectional view of the syringe of FIG. 1, with the stopped separated from the plunger, subsequent to an initial use.

Moving to FIG. 6, when it is desired to administer medication out from the syringe 10 and to a patient, the syringe 10 is actuated to its advanced position. The clinician may apply a distally directed force to the plunger assembly 14, such as by gripping and applying pressure on the flange 26 of syringe barrel 12 and the thumb press 44 on plunger 32, thereby causing the plunger 32 and stopper 34 to translate to the advanced position. As indicated above, in some embodiments, the amount of force required to move the plunger 32 and stopper 34 to the advanced position may need to be sufficient to overcome the frictional force between the annular rib 64 and the retaining ring 62. With the plunger assembly 14 being actuated to the advanced position, the nose member 52 of stopper 34 is pushed into the nozzle 28 of syringe barrel 12 and forms a seal therewith. Additionally, actuation of the plunger assembly 14 to the advanced position causes the cup member 50 of stopper 34 to be brought into forcible contact with the end wall 18 of syringe barrel 12. This forcible contact between the cup member 50 and the end wall 18 causes the cup member 50 to deflect from its concave shape to a generally flat shape and creates a suction force between the cup member 50 and the end wall 18. In some embodiments, a surface finish 68 (e.g., glossy finish) may be applied to the end wall 18 that promotes or enhances formation of a seal between the cup member 50 and the end wall 18, so as to create a strong suction therebetween.

Referring now to FIG. 7, in the event that an attempt is made to re-use the syringe 10—with a user trying to aspirate more medication into the syringe barrel 12 by drawing back the plunger assembly 14 to the retracted position—the syringe 10 automatically becomes disabled and such use is prevented. That is, as indicated above, the cup member 50 of stopper 34 is suctioned to the end wall 18 of syringe barrel 12 upon the plunger assembly 14 being actuated to the advanced position. This suction force between the cup member 50 and the end wall 18 is greater than a coupling force between the stopper 34 and the plunger 32 (e.g., between the flanged extension member 46 of plunger 32 and the receptacle 56 of stopper 34) and thus, when a proximally directed pulling force is applied to the plunger 32 that is greater than the coupling force, the stopper 34 becomes decoupled from the plunger 32—resulting in the separation of the stopper 34 and the plunger 32. The plunger 32 may thus being drawn back toward the retracted position when the proximally directed pulling force is applied thereto, but the stopper 34 remains suctioned to the end wall 18 of syringe barrel 12 and stays at the advanced positioned. Accordingly, the stopper 34 becomes trapped in the advanced positioned and the syringe 10 becomes disabled and unsuitable for re-use.

Beneficially, aspects of the disclosure described herein provide a single-use syringe that includes an automatic disabling feature incorporated therein. The automatic disabling feature prevents re-use of the syringe after an initial administering of medication out therefrom. The automatic disabling feature is included in the syringe at low cost, with no additional assembly steps required during manufacturing. A concave cup member included on the stopper of the syringe forms a suctioned engagement with a distal end wall of the syringe barrel when the plunger assembly of syringe is moved to an advanced position to administer medication to a patient. Once the cup member forms a suction with the end wall of the syringe barrel, any subsequent retraction of the plunger in the proximal direction will cause the plunger to separate from the stopper, with the stopper remaining at the distal end of the syringe barrel. With the stopper disconnected from the plunger and trapped at the distal end of the syringe barrel, the syringe is disabled and any re-use of the syringe in another injection application is prohibited.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A syringe comprising:
a syringe barrel having a barrel proximal end and a barrel distal end and defining a chamber configured for containing a fluid therein;

a plunger axially movable within the chamber of the syringe barrel, the plunger having a plunger proximal end and a plunger distal end; and a stopper detachably secured to the plunger distal end, the stopper axially movable with the plunger within the chamber, wherein the stopper includes:
an attachment member configured to detachably couple to the plunger distal end; and
a cup member extending out distally from the attachment member, the cup member composed of a flexible material and having a concave shape.

2. The syringe of claim 1, wherein the syringe barrel comprises:
a cylindrical outer wall extending between the barrel proximal end and the barrel distal end;
an end wall positioned at the barrel distal end; and
a nozzle extending distally from the end wall, the nozzle defining a lumen through which fluid enters into or exits from the chamber;
wherein an inner surface of the end wall comprises a generally flat surface, wherein upon application of a distal force to the plunger rod to an advanced position, the cup member is configured to be deflected and suctioned to the end wall.

3. The syringe of claim 1, wherein the cup member is deflectable between the concave shape and a flat shape and wherein when the plunger rod is in an advanced position, the cup member is deflected to the flat shape and is configured to suction to an end wall positioned at a barrel distal end.

4. The syringe of claim 3, wherein the stopper includes a nose member extending out distally past the cup member, the nose member positioned within a circumference of the cup member.

5. The syringe of claim 4, wherein the plunger, and the stopper coupled thereto, are movable from a retracted position where the cup member and the nose member are axially separated from the end wall to the advanced position where the cup member is in contact with the end wall and the nose member extends into the nozzle.

6. A syringe comprising:
a syringe barrel having a barrel proximal end and a barrel distal end and defining a chamber configured for containing a fluid therein;
a plunger axially movable within the chamber of the syringe barrel, the plunger having a plunger proximal end and a plunger distal end; and
a stopper secured to the plunger distal end, the stopper axially movable with the plunger within the chamber, wherein the stopper includes:
an attachment member configured to couple to the plunger distal end; and
a cup member extending out distally from the attachment member, the cup member having a concave shape, wherein
the syringe barrel comprises
a cylindrical outer wall extending between the barrel proximal end and the barrel distal end;
an end wall positioned at the barrel distal end; and
a nozzle extending distally from the end wall, the nozzle defining a lumen through which fluid enters into or exits from the chamber;
wherein an inner surface of the end wall comprises a generally flat surface;
wherein the cup member is deflectable between the concave shape and a flat shape;

wherein the stopper includes a nose member extending out distally past the cup member, the nose member positioned within a circumference of the cup member;

wherein the plunger, and the stopper coupled thereto, are movable from a retracted position where the cup member and the nose member are axially separated from the end wall to an advanced position where the cup member is in contact with the end wall and the nose member extends into the nozzle; and wherein with the plunger and the stopper in the advanced position, the nose member extends into the nozzle and the cup member deflects from the concave shape to the flat shape, thereby creating a suction between the stopper and the end wall of the syringe barrel.

7. The syringe of claim 6, wherein with the plunger and the stopper in the advanced position, the stopper is suctioned to the end wall with a suction force that is greater than a coupling force that couples the stopper to the plunger.

8. The syringe of claim 7, wherein the plunger distal end includes a flanged extension member and the attachment member of the stopper comprises a receptacle formed therein, with the flanged extension member coupling with the receptacle via a press fit connection, to secure the stopper to the plunger.

9. The syringe of claim 8, wherein with the stopper suctioned to the end wall with the suction force, the flanged extension member is pulled out of the receptacle when a proximally directed pulling force is applied to the plunger that is greater than the coupling force, thereby separating the stopper from the plunger.

10. The syringe of claim 9, wherein with the stopper separated from the plunger, the stopper is trapped at the advanced position, thereby preventing re-use of the syringe.

11. The syringe of claim 6, wherein the inner surface of the end wall includes a surface finish thereon that increases the suction between the cup member and the end wall.

12. The syringe of claim 5, wherein the syringe barrel comprises a retaining ring formed on an interior surface thereof, the retaining ring positioned toward the barrel proximal end, and wherein the plunger comprises an annular rib formed thereon positioned toward the plunger proximal end, with the annular rib proximal from the retaining ring when the plunger and the stopper are in the retracted position.

13. The syringe of claim 12, wherein to move the plunger and stopper to the advanced position, a distally directed force applied to the plunger must be greater than a friction force between the annular rib and the retaining ring.

14. A method of manufacturing the syringe of claim 1, the method comprising:

providing the syringe barrel;

securing the stopper to the plunger by detachably coupling the attachment member to the plunger distal end; and positioning the stopper and a portion of the plunger within the chamber of the syringe barrel;

wherein in positioning the stopper and the portion of the plunger within the chamber, the plunger and the stopper are put into an initial position, where the cup member is separated from the barrel distal end.

15. A syringe comprising:

a syringe barrel having a barrel proximal end and a barrel distal end and defining a chamber configured for containing a fluid therein; and a plunger assembly axially movable within the chamber of the syringe barrel between a retracted position and an advanced position, the plunger assembly including:

a plunger having a plunger proximal end and a plunger distal end; and a stopper secured to the plunger distal end, the stopper configured to suction to the barrel distal end upon the plunger assembly being moved to the advanced position;

wherein the stopper is further configured to separate from the plunger and remain suctioned to the barrel distal end upon the plunger being moved axially from the advanced position back toward the retracted position.

16. The syringe of claim 15, wherein the stopper comprises:

an attachment member configured to couple to the plunger distal end;

a cup member extending out distally from the attachment member, the cup member having a concave shape, with the cup member being deflectable between the concave shape and a flat shape; and a nose member extending out distally from the attachment member and past the cup member, the nose member positioned within a circumference of the cup member.

17. The syringe of claim 16, wherein the plunger distal end includes a flanged extension member and the attachment member of the stopper comprises a receptacle formed therein, with the flanged extension member coupling with the receptacle via a press fit connection, to secure the stopper to the plunger; and wherein, with the stopper suctioned to the barrel distal end, the flanged extension member is pulled out of the receptacle when the plunger is moved axially from the advanced position back to the retracted position.

18. The syringe of claim 16, wherein the syringe barrel comprises:

a cylindrical outer wall extending between the barrel proximal end and the barrel distal end; and an end wall positioned at the barrel distal end; and a nozzle extending distally from the end wall, the nozzle defining a lumen through which fluid enters into or exits from the chamber;

wherein an inner surface of the end wall comprises a generally flat surface.

19. The syringe of claim 18, wherein with the plunger assembly in the advanced position, the nose member extends into the nozzle and the cup member contacts the end wall and deflects from the concave shape to the flat shape, thereby suctioning the stopper to the end wall of the syringe barrel.

20. The syringe of claim 15, wherein the syringe barrel comprises a retaining ring formed on an interior surface thereof, the retaining ring positioned toward the barrel proximal end, and wherein the plunger comprises an annular rib formed thereon positioned toward the plunger proximal end, with the annular rib proximal from the retaining ring when the plunger and the stopper are in the retracted position; and wherein, to move the plunger and stopper to the advanced position, a distally directed force applied to the plunger assembly must be greater than a friction force between the annular rib and the retaining ring.

* * * * *